(12) United States Patent
Wang et al.

(10) Patent No.: US 7,947,191 B2
(45) Date of Patent: May 24, 2011

(54) COMPOSITE MATERIAL COMPOSED OF NANOPARTICLES OF TRANSITION METAL AND MAGNETIC FERRIC OXIDE, A METHODE OF PREPARING THE SAME, AND USES OF THE SAME

(75) Inventors: Yuan Wang, Beijing (CN); Junling Zhang, Beijing (CN); Minghui Liang, Beijing (CN); Xiaodong Wang, Beijing (CN); Yongge Wei, Beijing (CN); Linlin Gui, Beijing (CN)

(73) Assignee: Peiking University, Beijing (CN)

( * ) Notice: Subject to any disclaimer, the term of this patent is extended or adjusted under 35 U.S.C. 154(b) by 721 days.

(21) Appl. No.: 11/577,750

(22) PCT Filed: Oct. 12, 2005

(86) PCT No.: PCT/CN2005/001673
§ 371 (c)(1),
(2), (4) Date: Jul. 2, 2007

(87) PCT Pub. No.: WO2006/042453
PCT Pub. Date: Apr. 27, 2006

(65) Prior Publication Data
US 2009/0124834 A1    May 14, 2009

(30) Foreign Application Priority Data
Oct. 21, 2004  (CN) .......................... 2004 1 0086479

(51) Int. Cl.
*B01J 21/00* (2006.01)
(52) U.S. Cl. ............... 252/62.55; 252/62.56; 252/62.59; 977/773; 977/811
(58) Field of Classification Search ............... 252/62.55, 252/62.56, 62.59; 977/773, 811
See application file for complete search history.

(56) References Cited

U.S. PATENT DOCUMENTS

| 4,212,824 | A | * | 7/1980 | Seagraves ..................... 564/417 |
| 5,512,317 | A | * | 4/1996 | Blagev .......................... 427/215 |
| 6,514,481 | B1 | | 2/2003 | Prasad et al. |
| 2003/0104936 | A1 | * | 6/2003 | Mao et al. ..................... 502/339 |

FOREIGN PATENT DOCUMENTS

| CN | 1126526 | 7/1996 |
| CN | 1288779 | 3/2001 |
| CN | 1506407 | 6/2004 |

OTHER PUBLICATIONS

Seino et al., Gamma-ray synthesis of composite nanoparticles of noble metals and magnetic iron oxides, 2004, Scripta Materialia, 51, pp. 467-472.*

* cited by examiner

*Primary Examiner* — Steven Bos
(74) *Attorney, Agent, or Firm* — Gifford, Krass, Sprinkle, Anderson & Citkowski, P.C.

(57) ABSTRACT

A composite material composed of nanoparticles of transition metal(s) and magnetic ferric oxide, a method of preparing the same, and uses of the same are provided. The composite material is substantially composed of nanoparticles of transition metal(s) or alloy thereof and nanoparticles of magnetic ferric oxide, the size of nanoparticles of transition metal(s) or alloy thereof is in the range of 0.7 to 5 nm, the size of nanoparticles of magnetic ferric oxide is in the range of 5 to 50 nm, and the amount of transition metal(s) or alloy thereof is in the range of 0.1 to 30 wt %, based on the total weight of composite material, the magnetic ferric oxide is gamma-$Fe_2O_3$, $Fe_3O_4$, complex obtained from gamma-$Fe_2O_3$ by partial reduction, or complex obtained from $Fe_3O_4$ by partial reduction. The composite material has a high reactivity and an extreme selectivity for industrial reaction of hydrogenating halogeno-nitro-aromaticics to obtain halogeno-arylamine, and has important industrial applicability because the problem such as hydrogenolysis-dehalogenation during preparing halogeno arylamine by hydrogenating halogeno-nitro-aromatics is fully resolved by using the composite materials.

18 Claims, 1 Drawing Sheet

COMPOSITE MATERIAL COMPOSED OF NANOPARTICLES OF TRANSITION METAL AND MAGNETIC FERRIC OXIDE, A METHODE OF PREPARING THE SAME, AND USES OF THE SAME

TECHNICAL FIELD

This invention deals with a kind of nanocomposite materials composed of transition metal nanoclusters and magnetic iron oxides nanoparticles, their preparation methods and applications, especially the application as catalysts for the selectively catalytic hydrogenation of aromatic halonitro compounds to aromatic haloamines.

BACKGROUND TECHNOLOGY

Transition metal and alloy nanoclusters are nanoscopic materials with significant value of applications, which can be used to develop various functional materials and devices (Y Wang, Y. G Wei, "Metal Nanoclusters" (chapter) in: H. S, Nalwa (Ed.), *Encyclopedia of Nanoscience and Nanotechnology*, Vol. 5, pp. 337-367, 2004, American Scientific Publishers). The inventors of the present invention had invented a kind of "unprotected" noble metal and alloy nanoclusters, as well as the method for preparing the same.

These metal nanoclusters, stabilized only with simple ions and organic solvent molecules, have small particle sizes and narrow size distributions, and can be produced in a large scale. Moreover, the "unprotected" metal nanoclusters can be conveniently separated as precipitates from the original dispersions and purified, which can be then re-dispersed into many kinds of organic solvents to form stable metal colloidal solutions (Y. Wang, J. W. Ren, K. Deng, L. L. Gui, Y. Q. Tang, *Chem. Mater.*, 2000, 12, 1622; Chinese Patent, ZL 99100052.8). These metal nanoclusters have been used to synthesize catalysts (Y. Wang, et al., *J. Catal.*, 2004, 222, 493), catalytic electrodes for fuel cells (S. Mao, G Mao, "Supported Nanoparticle Catalyst", USA Patent, US 2003/0104936, A1, Jun. 5, 2003; Q. Xin, et al., *App. Catal. B*, 2003, 46, 273), and hydrogen sensors (Y. Wang, et al., *Chem. Mater.*, 2002, 14, 3953), etc.

$\gamma$-$Fe_2O_3$ and $Fe_3O_4$ are two kinds of well known magnetic iron oxides, both of them have the cubic inverse spinel crystal structure. They can transform to each other in specific conditions. For example, the oxidation of $Fe_3O_4$ at about 523 K can produce $\gamma$-$Fe_2O_3$, indicating that $\gamma$-$Fe_2O_3$ is more stable than $Fe_3O_4$. Different from the conventional ferromagnetic iron oxides materials with large particle sizes, upon decreasing the particle size to some extent, the iron oxides nanoparticles may exhibit special electronic, magnetic and optical properties. These unique properties endow the iron oxides nanoparticles with extensive application value in the fields of ultrahigh density data storage, bio-separation, controllable release of medicine, and wave-absorption materials. Currently, the most common method for industrial production of $\gamma$-$Fe_2O_3$ is firstly preparing the ferric hydroxide precursor, followed by calcining the precursor at high temperature resulting in $\alpha$-$Fe_2O_3$. $Fe_3O_4$ is then produced by the reduction of $\alpha$-$Fe_2O_3$ with reductive gases, and then oxidized to $\gamma$-$Fe_2O_3$ at high temperature. The required temperature in the preparation process is usually higher than 523 K. using $\gamma$-$Fe_2O_3$ and $Fe_3O_4$ materials prepared in such a high-temperature method, it is difficult to fabricate nanoscopic materials with small sizes and excellent performances.

The combination of metal nanoclusters and oxide nanoparticles can endow the composite materials with various properties. Many effective methods have been developed for immobilizing metal nanoclusters onto support particles, such as the impregnation method, reduction-deposition method, adsorption of protected metal colloidal particles, coordination capture method, deposition method, and the encapsulation method, etc. Due to the different microstructures of the metal-inorganic oxide composite materials derived from dissimilar preparation methods, catalysts with the same chemical compositions may exhibit obviously different catalytic properties. The composition, structure, particle size and size distribution of nanocomposites can also significantly affect their catalytic properties.

The immobilization of protected metal colloidal particles (Y. Wang, et al., *J. Chem. Soc. Chem. Commun*, 1989, 1878) or the encapsulation technique (C. Lange, et al., *Catal. Lett.*, 1999, 58, 207; A. Martino, et al., *J. Catal.*, 1999, 187, 30; A. G Sault et al., *J. Catal.*, 2000, 191, 474; H. Bönnemann, et al., *Eur: J. Inorg. Chem*, 2000, 5, 819; *Top. Catal.*, 2002, 18, 265; G. A. Somorjai, et al., *Chem. Mater.*, 2003, 15, 1242; J. Zhu, et al., *Langmuir*, 2003, 19, 4396) can be used to synthesize the metal-inorganic oxide nanocomposites. In the encapsulation technique, the inorganic oxides of alumina or silica, prepared by the in suit hydrolysis of the corresponding metal-alcohol salts $[M(RO)_n]$, are usually employed to encapsulate the metal colloidal particles protected by polymer, surfactant or coordination ligand. In order to obtain a close contact of the metal nanoparticles with inorganic supports, organic stabilizers originally adsorbed on the metal nanoclusters have to be removed by extraction or pyrolysis. This process may cause the aggregation of the metal nanoclusters, resulting in the difficulty in controlling the structure of the metal-inorganic oxide nanocomposites.

Seino et al. synthesized a kind of polyvinyl alcohol-metal-iron oxide magnetic nanocomposite materials by the photo-induced (using $\gamma$-irradiation) reduction of metal ions in aqueous solutions containing polyvinyl alcohol (PVA), and depositing the produced PVA-protected Au, Pt, Pd nanoclusters on commercially available $\gamma$-$Fe_2O_3$ particles with an average diameter of 26 nm or $Fe_3O_4$ particles with an average diameter of 100 nm (*Scripta Materalia*, 2004, 51, pp. 467-472). In this synthesis method, the concentration of iron oxides was relatively low (about 1 g/l), so the synthesis efficiency was not very high. On the other hand, the particle size of metal nanoclusters was dependent on the concentration of iron oxides particles. When $Fe_3O_4$ particles were used as the support, almost all of the metal particles deposited on the support were larger than 5 nm in size. In addition, the dispersion status of the oxide particles in the dispersion also affected the particle size of the deposited metal particles. Moreover, a part of PVA-protected Pt and Pd colloidal particles could not be adsorbed onto the iron oxides support.

Aromatic haloamines are important organic intermediates in the synthesis of dyes, pesticides, herbicides, medicines and special polymer materials. The hydrogenation of aromatic halonitro compounds to corresponding aromatic haloamines is one of important processes of chemical industry. It is a challenge in this synthesis industry to prevent the hydrogenolysis of the carbon-halogen bond in the haloaromatics, while maintaining the high catalytic activity of the catalysts for the hydrogenation of the aromatic halonitro compounds, especially when the conversion of the substrates is near 100%. If other electron-donating groups exist in the aromatic ring of the products, the hydrodehalogenation would become more serious (R. J. Maleski, et al., Eastman Chemical Co.) U.S. Pat. No. 6,034,276, (2000, 3, 7), WO 00/56698, 2000, 9, 2).

Over traditional metal catalysts (for example, Pt/C, Pd/C or Raney Ni), the hydrogenation of aromatic halonitro compounds was always companied by the hydrodehalogenation side reaction. Dehalogenation in the hydrogenation of bromine- or iodine-substituted aromatic nitro compounds is more serious than that in the case of aromatic chloronitro compounds. The order of susceptibility to hydrogenolysis for halogen-carbon bonds in aromatic halonitro compounds is I>Br>Cl>F (J. R. Kosak, in: *Catalysis in Organic Syntheses*, Academic Press, New York, 1980, pp. 107-117).

JP 2004277409-A (MITSUI CHEM. INC., JAPAN, 2004), disclose a technique for suppressing the hydrodechlorination of ortho-chloroaniline (o-CAN) over a Pt/C catalyst by charging 9.8 MPa of $CO_2$ into the reaction system, which achieve a selectivity of 99.7 mol % to O-CAN. Obviously, this technology need highly expensive reactors, and could not completely suppress the dechlorination side reaction.

Over a $Pt/TiO_2$ catalyst in a strong metal-support interaction state, the selective hydrogenation of para-chloronitrobenzene (p-CNB) was investigated under atmosphere pressure. When the conversion of p-CNB was less than 99.7%, the selectivity to para-chloroaniline (p-CAN) could reach 99.3%, which was the best selectivity in publications over Pt-based heterogeneous catalysts (B. Coq, A. Tijani, R. Dutartre, F. Figueras, *J. Mol. Catal. A*, 1993, 79, 253). However, after the complete conversion of the p-CNB substrate, the dechlorination rate of p-CAN increased rapidly. It is difficult to precisely control the reaction process in industrial production; thereby it is difficult to efficiently produce aromatic haloamines with high purity by using this catalyst.

Adding dechlorination inhibitors into the reaction system is also a method for suppressing the hydrodechlorination side reaction. EP473552-A (Baurmeister, et al., 1992) described that in the hydrogenation of 2,4-dinitrochlorobenzene (2,4-DNCB) over a Pt/C catalyst modified with formamidine acetate, the selectivity to 4-chloro-m-phenylenediamine (4-CPDA) could reach 98% at complete conversion of the substrate.

DESCRIPTION OF THE INVENTION

The purpose of the present invention is providing a kind of nanocomposite materials composed of transition metals nanoclusters and magnetic iron oxides nanoparticles, and their preparation methods.

The invented transition metals-magnetic iron oxides nanocomposite materials are essentially composed of transition metals or their alloys nanoparticles with particle sizes ranging from 0.7 to 5 nm and magnetic iron oxides nanoparticles having sizes ranging from 5 to 50 nm. The total contents of the related transition metals or alloys in the related nanocomposite materials range from 0.1-30 wt. %. The related magnetic iron oxides include $\gamma$-$Fe_2O_3$, $Fe_3O_4$, the composite derived from part reduction of $\gamma$-$Fe_2O_3$, or the composite derived from part oxidation of $Fe_3O_4$.

The said composite derived from part reduction of $\gamma$-$Fe_2O_3$ was obtained by partly reducing the related transition metal-$\gamma$-$Fe_2O_3$ nanocomposite at 278-473 K in the presence of the reductants including hydrogen, glycolic acid, alcohol, aldehyde, etc. The said composite derived from part oxidation of $Fe_3O_4$ was obtained by partly oxidating the related transition metal-$Fe_3O_4$ nanocomposite at 313-523 K in the presence of oxygen.

In the present invention, typical transition metals are selected from Pt, Ru, Rh or Ir, etc. Typical transition metal alloys are selected from discretional two or more elements of Pt, Pd, Rh, Ru, Ir and Os. Typical particle sizes of the related magnetic iron oxides nanoparticles range from 5 to 25 nm.

The invented transition metals-magnetic iron oxides nanocomposite materials can be prepared by the following two methods:

The first method comprises the steps of:

1) preparing transition metal colloids: dissolving at least one kinds of soluble salts or acids containing the related transition metals into an alcohol solution or alcohol/water mixture to form a solution of transition metal compounds with concentration of 0.01-100 g/l, and adding an alcohol solution, or aqueous solution, or alcohol/water mixture of alkali metal hydroxides or alkaline-earth metal hydroxides into the said solution of the transition metal compounds, then heating the obtained mixture at 343-473 K to produce a colloidal solution of transition metal nanoclusters. The typical molar ratio of alkali metal hydroxides or alkaline-earth metal hydroxides to the salts or acids containing the said transition metals is in the range from 3 to 30. Typical alcohols are selected from alcohols containing one, or tow, or three hydroxyl groups and 1-8 carbon atoms, and unitary methoxyl or ethoxyl derivatives of the alcohols containing two or three hydroxyl groups and 1-8 carbon atoms. The typical volume content of water in the alcohol/water mixtures is 0-50%;

2) preparing ferric hydroxide colloids: forming a precipitate of ferric hydroxide by adding an alkaline solution into a solution containing ferric ($Fe^{3+}$) salts to adjust the pH value to 4-12, and peptizing the obtained precipitate in peptizing agents to produce a colloidal solution of ferric hydroxide with a concentration of 1-300 g/l. The said peptizing agents are selected from ferric chloride solution, ferric nitrate solution and hydrochloric acid;

3) preparing nanocomposite materials composed of transition metals nanoclusters and magnetic iron oxides nanoparticles: mixing the transition metal colloidal solutions prepared in step 1) and the ferric hydroxide colloidal solutions prepared in step 2) at mass ratios of metal colloidal solution to ferric hydroxide colloidal solution of 1:3-1:13400, and heat treating the mixture at 313-523 K for 1-200 h, then drying the obtained precipitates at 278-523 K to provide the related nanocomposite materials composed of transition metals nanoclusters and magnetic iron oxides nanoparticles.

The second method comprises the steps of:

1) preparing transition metal colloids: (A) dissolving at least one kinds of soluble salts or acids containing the related transition metals into an alcohol solution or alcohol/water mixture to form a solution of transition metal compounds with concentration of 0.01-100 g/l, and adding an alcohol solution, or aqueous solution, or alcohol/water mixture of alkali metal hydroxides or alkaline-earth metal hydroxides into the said solution of the transition metal compounds. The typical molar ratio of alkali metal hydroxides or alkaline-earth metal hydroxides to the salts or acids containing the said transition metals is in the range from 3 to 30. Typical alcohols are selected from alcohols containing one, or tow, or three hydroxyl groups and 1-8 carbon atoms, and unitary methoxyl or ethoxyl derivatives of the alcohols containing two or three hydroxyl groups and 1-8 carbon atoms. The typical volume content of water in the alcohol/water mixtures is 0-50%; (B) heating the obtained mixture at 343-473 K, and adding an acidic aqueous solution to form a precipitate of transition metal nanoclusters, then dispersing the said precipitate into ethylene glycol solutions of alkali metal or alkaline-earth metal hydroxides, or into organic solvents, to produce a colloidal solution of transition metal nanoclusters. Typical organic solvents are selected from alcohols containing tow or three hydroxyl groups and 1-8 carbon atoms, ketone, 1,4-dioxane, DMSO, THF and DMF;

2) preparing ferric hydroxide colloids: forming a precipitate of ferric hydroxide by adding an alkaline solution into a solution containing ferric ($Fe^{3+}$) salts to adjust the pH value to 4-12, and peptizing the obtained precipitate in peptizing agents to produce a colloidal solution of ferric hydroxide with a concentration of 1-300 g l. The said peptizing agents are selected from ferric chloride solution, ferric nitrate solution and hydrochloric acid;

3) preparing nanocomposite materials composed of transition metals nanoclusters and magnetic iron oxides nanoparticles: mixing the transition metal colloidal solutions prepared in step 1) and the ferric hydroxide colloidal solutions prepared in step 2) at mass ratios of metal colloidal solution to ferric hydroxide colloidal solution of 1:3-1:13400, and adding one or several kinds of organic reductants into the mixture, then heat treating the said mixture at 313-523 K for 1-200 h, followed by drying the obtained precipitate at 278-523 K to provide the related nanocomposite materials composed of transition metals nanoclusters and magnetic iron oxides nanoparticles. The related organic reductants are selected from formaldehyde, glycolic acid, sodium glycolate, isopropyl alcohol, glyoxal, oxalic acid and hydrogen. The typical molar ratio of organic reductants to ferric hydroxide is 0.1-10.

In the two preparation methods described above, soluble salts or acids containing the related transition metals in step 1) are selected from salts or acids containing Pt, Pd, Ru, Rh, Os and Ir.

In step 2), the concentration of the related $Fe^{3+}$ salts in the solutions is 0.01-4 mol/l; the ferric salts are selected from ferric sulfate, ferric nitrate, ferric chloride, etc. Typical alkalis include ammonia, potassium hydroxide, sodium hydroxide, lithium hydroxide, tetramethylammonium hydroxide, etc; the typical temperature for precipitating ferric hydroxide is 278-370 K; typical concentration of peptizing agents is in the range of 0.01-2 mol/l; typical peptization temperature is 278-373 K.

In step 3), the heat treating methods include solvothermal method, beating and refluxing method, and microwave irradiation method; the drying processes can be conducted in the following manners: drying in vacuum can provide the nanocomposite materials composed of transition metal nanoclusters and $Fe_3O_4$ nanoparticles; oxidation drying in oxygen-containing atmosphere can provide the nanocomposite materials composed of transition metal nanoclusters and $\gamma$-$Fe_2O_3$ nanoparticles; part-oxidation drying in oxygen-containing atmosphere can provide the nanocomposite materials composed of transition metal nanoclusters and magnetic iron oxides nanoparticles, the said magnetic iron oxides are the composite produced by partly oxidating $Fe_3O_4$ in the transition metal-$Fe_3O_4$ nanocomposite. Moreover, the related nanocomposite materials composed of transition metal nanoclusters and magnetic iron oxides nanoparticles can also be obtained by partly reducing the transition metal-$\gamma$-$Fe_2O_3$ nanocomposite materials at 278-473 K in the presence of the reductants selected from hydrogen, glycolic acid, alcohol and aldehyde, the said magnetic iron oxides are the composite produced by partly reducing $\gamma$-$Fe_2O_3$ in the transition metal-$\gamma$-$Fe_2O_3$ nanocomposite materials.

The other purpose of the present invention is to provide the application of the invented transition metals-magnetic iron oxides nanocomposite materials.

Studies of the inventors of the present invention showed that the nanocomposite materials composed of the transition metal nanoclusters and magnetic iron oxides nanoparticles exhibited excellent catalytic properties, especially the high catalytic activity and superior selectivity in the selective hydrogenation of aromatic halonitro compounds. Moreover, the magnetic property of the nanocomposite material provides a convenient route for separating the catalysts from the reaction system in an applied magnetic field.

Over the invented nanocomposite catalysts, the hydrogenation of many aromatic halonitro compounds, such as halonitrobenzenes, halodinitrobenzenes and halonitrobiphenyl, can be conducted with very high selectivity, i.e. the hydrodehalogenation of the corresponding aromatic haloamine products would not occur over these catalysts. Generally, the hydrogenation conditions are as follows: temperature, 273-393 K; pressure of hydrogen, 0.1-10 MPa. The typical solvents used in the hydrogenation can be selected from alcohols or other organic solvents such as THF, DMSO and toluene. When the reaction is complete, the catalyst can be recovered from the reaction system by magnetic separation, centrifugation or filtration, and be reused.

The typical structures of aromatic halonitro compounds mentioned above are shown as follows:

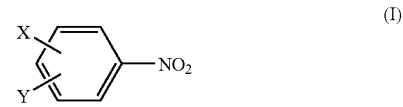
(I)

In Scheme (I), X=Cl, Br or I; Y=H, R, COOR, RO, Cl, Br, I, $NO_2$ or $NH_2$ (R is saturated alkyl of $C_1$-$C_4$);

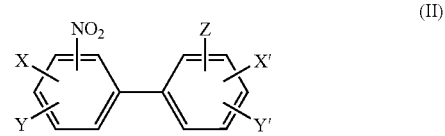
(II)

In Scheme (II), X=Cl, Br or I; X', Y, Y'=H, R, COOR, RO, Cl, Br or I; Z=H, $NO_2$ or $NH_2$ (R is saturated alkyl of $C_1$-$C_4$).

EXAMPLES

Objects and advantages of this invention are further illustrated by the following examples, but the particular materials and amounts thereof recited in these examples, as well as other conditions and details, should not be construed to unduly limit this invention.

Section 1

Examples for the Preparation of Nanocomposite Materials

Example 1

Preparation of Pt/γ-$Fe_2O_3$ Nanocomposite with 1 wt. % of Pt Loading 1.0 g of hexachloroplatinate hexahydrate ($H_2PtCl_6 \cdot 6H_2O$) was dissolved into 50 ml of ethylene glycol (EG), followed by addition of 50 ml of EG solution containing NaOH (0.5 mol/l). After stirring at room temperature for 5 min, the mixture was refluxed at 453 K for 3 h, with a nitrogen flow passing through the reaction system. A homogeneous, dark-brown colloidal solution of "unprotected" Pt nanoclusters (Pt: 3.75 g/l) was obtained. The average diameter of the prepared Pt nanoclusters was determined to be 2.0 nm by TEM measurements.

An aqueous solution of ammonia (10%) was added dropwise into a solution of ferric chloride ($FeCl_3$) in 100 ml of water (4%) to adjust the pH value to about 7.5, after ageing for 5 min, the produced precipitate of ferric hydroxide was filtered, washed to remove $Cl^-$, and peptized in 30 ml of an aqueous solution of $FeCl_3$ (4%) by stirring and slightly heating under 323 K, resulting in a colloidal solution of ferric hydroxide, which was kept at room temperature for utilization.

2.6 ml of the Pt colloidal solution was added dropwise into the prepared ferric hydroxide colloidal solution under stirring. The mixture was then heated in a Teflonlined autoclave at 353 K for 72 h. A magnetic precipitate was produced, which was separated by filtration, washed to remove $Cl^-$, dried and oxidized at 353 K in air for 48 h to produce the Pt/γ-$Fe_2O_3$ nanocomposite containing 1 wt. % of Pt. The average diameter of γ-$Fe_2O_3$ nanoparticles was determined to be 16 nm by TEM.

Figure 1:
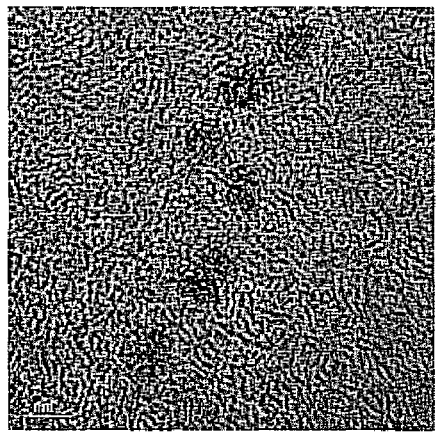
FIG. 1 is a transmission electron microscope (TEM) image of Pt nanoclusters (Example 1).
Figure 2:
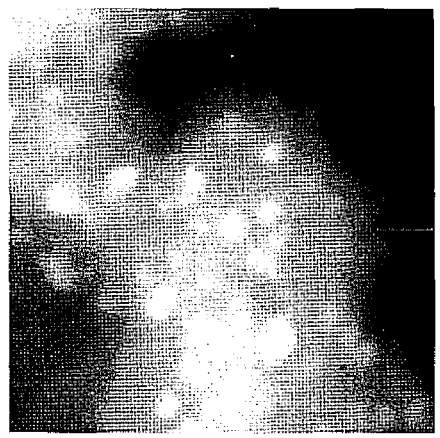
FIG. 2 is a scanning transmission electron microscope (STEM) image of the Pt/$\gamma$-$Fe_2O_3$ nanocomposite according to the present invention (Example 1).
Figure 3:
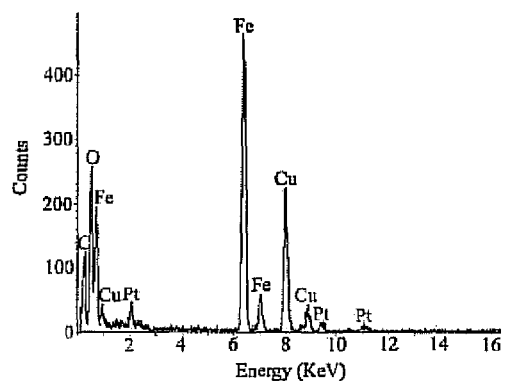
FIG. 3 is an energy dispersive X-ray (EDX) pattern of the Pt/$\gamma$-$Fe_2O_3$ nanocomposite according to the present invention (Example 1).
Figure 4:
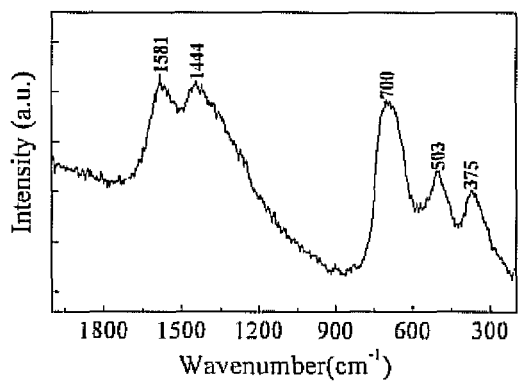
FIG. 4 is a Raman spectrum of the Pt/$\gamma$-$Fe_2O_3$ nanocomposite according to the present invention (Example 1).

FIG. 1 shows the TEM image of the Pt nanoclusters prepared in Example 1. FIG. 2 shows the STEM image of the Pt/γ-$Fe_2O_3$ nanocomposite containing 1 wt. % of Pt. FIG. 3 shows the EDX pattern of the Pt/γ-$Fe_2O_3$ nanocomposite containing 1 wt. % of Pt. The above characterization results illustrated that the Pt nanoclusters were well dispersed in the matrix of the γ-$Fe_2O_3$ nanoparticles without obvious aggregation. FIG. 4 shows the Raman spectrum of the Pt/γ-$Fe_2O_3$ nanocomposite containing 1 wt. % of Pt, demonstrating that iron oxide in the nanocomposite is γ-$Fe_2O_3$.

Example 2

Preparation of Pt/γ-$Fe_2O_3$ Nanocomposite with 30 wt. % of Pt Loading 1.0 g of $H_2PtCl_6 \cdot 6H_2O$ was dissolved into 50 ml of EG, followed by addition of 125 ml of EG/$H_2O$ (4:1, v:v) solution containing $Ba(OH)_2$ (0.1 mol/l). After stirring at room temperature for 5 min, the mixture was refluxed at 433 K for 3 h under flowing nitrogen to produce a colloidal solution of "unprotected" Pt nanoclusters (Pt: 3.75 g/l). The average diameter of the obtained Pt nanoclusters is 3.0 nm.

An aqueous solution of ammonia (10%) was added dropwise into a solution of $FeCl_3$ in 100 ml of water (4%) to adjust the pH value to about 8.0, after ageing for 3 min, the produced precipitate of ferric hydroxide was then filtered, washed to remove $Cl^-$, and peptized in 30 ml of an aqueous solution of $FeCl_3$ (4%) by stirring and slightly heating under 323 K, resulting in a colloidal solution of ferric hydroxide, which was kept at room temperature for utilization.

78.0 ml of the Pt colloidal solution was added dropwise into the prepared ferric hydroxide colloidal solution under stirring. The mixture was then heated in a Teflonlined autoclave at 353 K for 72 h. A magnetic precipitate was produced, which was separated by filtration, washed to remove $Cl^-$, and dried at 353 K in air for 48 h to produce the Pt/γ-$Fe_2O_3$ nanocomposite containing 30 wt. % of Pt. Particle size analyses showed that the average diameter of γ-$Fe_2O_3$ nanoparticles is 9 nm.

Example 3

Preparation of Pt/$Fe_3O_4$ Nanocomposite with 3 wt. % of Pt Loading

Figure 5:
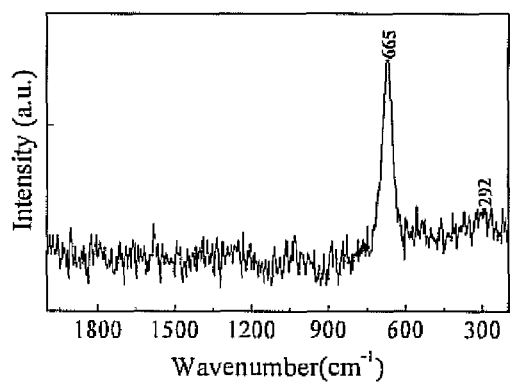
FIG. 5 is a Raman spectrum of the Pt/$Fe_3O_4$ nanocomposite according to the present invention (Example 3).

Colloidal solutions of Pt nanoclusters and ferric hydroxide nanoparticles were prepared as in Example 1. The Pt/$Fe_3O_4$ nanocomposite was prepared as follows: 7.8 ml of the Pt colloidal solution was added dropwise into 30 ml of the ferric hydroxide colloidal solution under stirring. The mixture was then heated in a Teflonlined autoclave at 353 K for 72 h. A magnetic precipitate was produced, which was separated by a filtration, washed to remove $Cl^-$, and dried at 353 K in vacuum to produce the Pt/$Fe_3O_4$ nanocomposite containing 3 wt. % of Pt. Particle size analyses showed that the average diameter of $Fe_3O_4$ nanoparticles is 16 nm. FIG. 5 shows the Raman spectrum of the Pt/$Fe_3O_4$ nanocomposite containing 3 wt. % of Pt, indicating that iron oxide in the nanocomposite is $Fe_3O_4$.

Example 4

Preparation of Pt/$Fe_3O_4$ Nanocomposite with 0.1 wt. % of Pt Loading 0.1 g of $H_2PtCl_6 \cdot 6H_2O$ was dissolved into 50 ml of EG, followed by addition of 50 ml of EG solution containing NaOH (0.05 mol/l). After stirring at room temperature for 5 min, the mixture was refluxed at 433 K for 3 h to produce a colloidal solution of "unprotected" Pt nanoclusters (Pt: 0.375 g/l). Particle size analyses showed that the average diameter of the obtained Pt nanoclusters is 1.0 nm.

An aqueous solution of ammonia (10%) was added dropwise into a solution of $FeCl_3$ in 200 ml of water (2%) to adjust the pH value to about 12, after ageing for 10 min, the produced precipitate of ferric hydroxide was then separated by filtration, washed to remove $Cl^-$, and peptized in 60 ml of an aqueous solution of $FeCl_3$ (2%) by stirring and heating under 363 K, resulting in a colloidal solution of ferric hydroxide, which was kept at room temperature for utilization.

2.6 ml of the Pt colloidal solution was added dropwise into the ferric hydroxide colloidal solution under stirring. The mixture was then heated in a Teflonlined autoclave at 413 K for 160 h. A magnetic precipitate was produced, which was separated by filtration, washed to remove $Cl^-$, and dried in vacuum for 48 h to produce the Pt/$Fe_3O_4$ nanocomposite containing 0.1 wt. % of Pt. Particle size analyses showed that the average diameter of $Fe_3O_4$ is 45 nm.

Example 5

Preparation of Ru/γ-$Fe_2O_3$ Nanocomposite with 1 wt. % of Ru Loading 1.0 g of $RuCl_3 \cdot 3H_2O$ was dissolved into 50 ml of ethylene glycol monomethyl ether, followed by addition of 50 ml of EG/H$_2$O (1:1, v:v) solution containing KOH (0.5 mol/l). After stirring at room temperature for 5 min, the mixture was refluxed at 373 K for 3 h to produce a colloidal solution of "unprotected" Ru nanoclusters (Ru: 3.75 g/l). Particle size analyses showed that the average diameter of the obtained Ru nanoclusters is 1.3 nm.

An aqueous solution of tetramethylammonium hydrate (10%) was added dropwise into a solution of ferric nitrate in 150 ml of water (4%) to adjust the pH value to about 4, after ageing for 3 min, the produced precipitate of ferric hydroxide was then separated by filtration, washed, and peptized in 30 ml of a dilute aqueous solution of HCl (1%) by stirring and slightly heating under 333 K, resulting in a colloidal solution of ferric hydroxide, which was kept at room temperature for utilization.

2.6 ml of the Ru colloidal solution was added dropwise into the ferric hydroxide colloidal solution under stirring. The mixture was then heated in a Teflonlined autoclave at 313 K for 72 h. A black precipitate was produced, which was separated by filtration, washed to remove Cl$^-$, dried and oxidized at 353 K in air for 48 h to produce the Ru/γ-Fe$_2$O$_3$ nanocomposite containing 1 wt. % of Ru. Particle size analyses showed that the average diameter of γ-Fe$_2$O$_3$ nanoparticles is 6 nm.

Example 6

Preparation of Pt/γ-Fe$_2$O$_3$ Nanocomposite with 5 wt. % of Pt Loading

Colloidal solutions of Pt nanoclusters and ferric hydroxide nanoparticles were prepared as in Example 1. The Pt/γ-Fe$_2$O$_3$ nanocomposite was prepared as follows: 13 ml of an aqueous solution of HCl (1 mol/l) was added into 13.1 ml of the Pt colloidal solution (3.75 g/l) to form a precipitate of the Pt nanoclusters, which was separated by centrifugation and then redispersed into 5.6 ml EG solution of NaOH (0.5 mol/l), followed by the addition of 0.3 g glycolic acid. The obtained colloidal solution of Pt nanoclusters was added dropwise into 30 ml of the ferric hydroxide colloidal solution under vigorously stirring, the mixture was refluxed at 373 K for 72 h. The produced black precipitate was filtered, washed, dried and oxidized at 353 K in air for 48 h to produce the Pt/γ-Fe$_2$O$_3$ nanocomposite containing 5 wt. % of Pt. Calcining the obtained sample at 773 K for 2 h to produce the calcined Pt/γ-Fe$_2$O$_3$ nanocomposite containing 5 wt. % of Pt. X-ray diffraction (XRD) patterns and other measurements demonstrated that iron oxide in the nanocomposite is γ-Fe$_2$O$_3$.

Example 7

Preparation of Pt/Magnetic Iron Oxides Nanocomposite with 3 wt. % of Pt Loading

Colloidal solutions of Pt nanoclusters and ferric hydroxide nanoparticles were prepared as in Example 1. The Pt/magnetic iron oxides nanocomposite was prepared as follows: 7.8 ml of the Pt colloidal solution (3.75 g/l) was added into 30 ml of the ferric hydroxide colloidal solution under stirring. The mixture was then heated and refluxed under N$_2$ for 24 h. The obtained precipitate was filtered, washed, dried and oxidized at 333 K in air for 12 h to produce the nanocomposite composed of Pt/γ-Fe$_2$O$_3$ and Pt/Fe$_3$O$_4$ with 3 wt. % of Pt loading. Raman spectra proved that the nanocomposite consisted of γ-Fe$_2$O$_3$ and Fe$_3$O$_4$.

Example 8

Preparation of Pt/Fe$_3$O$_4$ Nanocomposite with 6 wt. % of Pt Loading

Colloidal solutions of Pt nanoclusters and ferric hydroxide nanoparticles were prepared as in Example 1. The Pt/Fe$_3$O$_4$ nanocomposite was prepared as follows: 15 ml of an aqueous solution of HCl (1 mol/l) was added into 15.6 ml of the Pt colloidal solution (3.75 g/l) to produce a precipitate of the Pt nanoclusters, which was separated by centrifugation and then redispersed into 9 ml THF solution of KOH (0.1 mol/l). The obtained colloidal solution of Pt nanoclusters was added dropwise into 30 ml of the ferric hydroxide colloidal solution under vigorously stirring, followed by the addition of 10 ml THF solution containing 0.5 g of sodium glycolate. The mixture was heated by microwave irradiation under stirring for 2 h. The product was filtered, washed, and dried at 353 K in vacuum for 24 h to produce the Pt/Fe$_3$O$_4$ nanocomposite containing 6 wt. % of Pt.

Example 9

Preparation of Pt—Ru/γ-Fe$_2$O$_3$ Nanocomposite with 1 wt. % of Metal Loading and a Pt/Ru Molar Ratio of 1:1

0.5179 g of H$_2$PtCl$_6$.6H$_2$O and 0.2073 g of RuCl$_3$.3H$_2$O were dissolved into 25 ml of EG, followed by the addition of 25 ml EG solution containing NaOH (1.0 mol/l). After stirring at room temperature for 5 min, the mixture was refluxed at 453 K for 3 h to produce a colloidal solution of "unprotected" Pt—Ru alloy nanoclusters, wherein the total metal concentration of Pt—Ru is 5.92 g/l.

An aqueous solution of ammonia (10%) was added dropwise into a solution of FeCl$_3$ in 2.5 ml of water (10 mol/l) to adjust the pH value to about 7.5, after ageing for 5 min the produced precipitate of ferric hydroxide was then filtered, washed to remove Cl$^-$, and peptized in 30 ml aqueous solution of FeCl$_3$ (1 mol/l) by stirring and slightly heating, resulting in a colloidal solution of ferric hydroxide, which was kept at room temperature for utilization.

1.65 ml of the Pt—Ru alloy colloidal solution was added into the ferric hydroxide colloidal solution under stirring. The mixture was then heated in a Teflonlined autoclave at 393 K for 72 h. A black precipitate was produced, which was filtered, washed, dried and oxidized at 393 K in air for 48 h to produce the Pt—Ru/γ-Fe$_2$O$_3$ nanocomposite with 1 wt. % of metal loading and a Pt/Ru molar ratio of 1:1.

Example 10

Preparation of Pt—Ir/γ-Fe$_2$O$_3$ Nanocomposite with 1 wt. % of Metal Loading and a Pt/Ir Molar Ratio of 1:1

0.5179 g of H$_2$PtCl$_6$.6H$_2$O and 0.2986 g of IrCl$_3$.3H$_2$O were dissolved into 50 ml glycerol, followed by the addition of 50 ml glycerol solution containing NaOH (0.6 mol/l). After stirring at room temperature for 5 min, the mixture was refluxed at 453 K for 3 h to produce a colloidal solution of "unprotected" Pt—Ir alloy nanoclusters, wherein the metal total concentration of Pt—Ir is 3.87 g/l.

An aqueous solution of KOH (2%) was added dropwise into a solution of FeCl$_3$ in 25 ml of water (1 mol/l) to adjust the pH value to about 7.53 after ageing for 5 min, the produced precipitate of ferric hydroxide was then filtered, washed to remove Cl⁻, and peptized in 30 ml aqueous solution of $FeCl_3$ (4%) by stirring at room temperature, resulting in a colloidal solution of ferric hydroxide.

2.52 ml of the Pt—Ir alloy colloidal solution was added dropwise into the ferric hydroxide colloidal solution under stirring. The mixture was then heated in a Teflonlined autoclave at 353 K for 72 h. A black precipitate was produced, which was filtered, washed to remove Cl⁻, dried and oxidized at 423 K in air for 48 h to produce the Pt—Ir/$\gamma$-$Fe_2O_3$ nanocomposite with 1 wt. % of metal loading and a Pt/Ir molar ratio of 1:1.

Example 11

Preparation of Rh/$\gamma$-$Fe_2O_3$ Nanocomposite with 1 wt. % of Rh Loading

Replacing $H_2PtCl_6.6H_2O$ in Example 1 with $RhCl_3.3H_2O$ of the same molar content, and using the same preparation method to produce the Rh/$\gamma$-$Fe_2O_3$ nanocomposite containing 1 wt. % of Rh.

Example 12

Preparation of Pt—Pd/$\gamma$-$Fe_2O_3$ Nanocomposite with 1 wt. % of Metal Loading and a Pt/Pd Molar Ratio of 4:1

Replacing $RuCl_3.3H_2O$ in Example 9 with $PdCl_2.xH_2O$, keeping the Pt/Pd molar ratio to be 4:1, and using the same preparation method to produce the Pt—Pd/$\gamma$-$Fe_2O_3$ nanocomposite with 1 wt. % of metal loading and a Pt/Pd molar ratio of 4:1.

Example 13

Preparation of Pt/Magnetic Iron Oxide Nanocomposite

Heating the red-brown Pt/$\gamma$-$Fe_2O_3$ nanocomposite containing 1 wt. % of Pt prepared in Example 1 at 333 K under hydrogen for 60 min to produce a black Pt/magnetic iron oxide nanocomposite. Raman analyses revealed that the obtained nanocomposite consisted of $\gamma$-$Fe_2O_3$ and $Fe_3O_4$.

Selecting two or several kinds of soluble salts of Pt, Rh, Ru, Ir, Os and Pd, and adopting the similar methods as described in Example 1-13, can prepare nanocomposite materials composed of alloy nanoclusters of the selected transition metals and the magnetic iron oxides nanoparticles.

Section 2

Examples for the Application of Nanocomposite Materials in Catalysis

The nanocomposite materials composed of transition metal nanoclusters and magnetic iron oxides nanoparticles according to the present invention exhibited high catalytic activity, excellent stability and superior selectivity in the hydrogenation of chlorine-, bromine-, and iodine-substituted aromatic nitro compounds (such as halonitrobenzenes and halonitrobiphenyl containing several kinds of substituted groups) to the corresponding aromatic haloamines. Over the invented nanocomposite catalysts, the selectivities to the corresponding aromatic haloamines can reach a level higher than 99.9% at 100% conversion of the aromatic halonitro compounds. It should be pointed out that even when the aromatic halonitro compounds were completely exhausted in these catalytic reactions, the coexistence of the present nanocomposite catalysts and the aromatic haloamines products under 0.1-4.0 MPa of hydrogen pressure will not cause the decrease in the selectivity to the desirable products. In other words, over these nanocomposite catalysts, the hydrodehalogenation side reactions in the catalytic reactions of interest are complete inhibited. Due to the fully suppression of the dehalogenation side reaction, the hydrogenation of the aromatic halonitro compounds can be conducted rapidly and completely under elevated hydrogen pressure, actualizing the aim of efficiently producing the corresponding aromatic haloamines with a high purity. Meanwhile, the separation process of the reaction products is also facilitated. The magnetic or super-paramagnetic property of the nanocomposite catalysts provides a convenient route for separating the catalysts from the reaction systems in an applied magnetic field.

In typical catalytic hydrogenation experiments, the invented magnetic transition metal-iron oxides nanocomposite materials were dispersed in suitable volume of organic solvents, activated under hydrogen ambience. Then organic solutions of the aromatic halonitro compound were added into the reactor to start the reaction. The obtained products were analyzed by gas chromatography (GC). After the reaction was complete, the catalyst was separated from the reaction system in an applied magnetic field and washed before reusing in the next cycle of the reaction. The catalyst separation can also be conducted by the conventional methods such as filtration or centrifugation. The reaction temperature was in a range from 273 to 393 K, and the pressure of hydrogen ranged from 0.1 to 10 MPa.

Example 14

Selective hydrogenation of o-chloronitrobenzene (o-CNB) over Pt/$\gamma$-$Fe_2O_3$ 1) Reaction Under 0.1 MPa of Hydrogen Pressure The reaction was carried out in a 50-ml reactor with magnetic stirring at 333 K. Prior to the reaction, air in the system was replaced by hydrogen. 0.2 g of the Pt/$\gamma$-$Fe_2O_3$ nanocomposite containing 1 wt. % of Pt prepared in Example 1 was dispersed in 5 ml of methanol, and activated at 333 K under 0.1 MPa of hydrogen pressure for 30 min, then 20 ml of a methanol solution containing 13.0 mmol of o-CNB was added into the reactor to start the reaction. The products were analyzed by GC.

2) Reaction Under 2.0 MPa of Hydrogen Pressure 0.05 g of the Pt/$\gamma$-$Fe_2O_3$ nanocomposite containing 1 wt. % of Pt and 13.0 mmol of o-CNB were added into 25 ml of methanol in an autoclave, then the reaction was conducted at 333 K under 2.0 MPa of hydrogen pressure. The products were analyzed by GC.

3) Reaction Under 4.0 MPa of Hydrogen Pressure 0.05 g of the Pt/$\gamma$-$Fe_2O_3$ nanocomposite containing 1 wt. % of Pt and 13.0 mmol of o-CNB were added into 25 ml of methanol in an autoclave, then the reaction was conducted at 333 K under 4.0 MPa of hydrogen pressure. The products were analyzed by GC.

The catalytic activity and selectivity over the catalyst are listed in TABLE 1.

TABLE 1

| $H_2$ pressure (MPa) | Catalyst (g) | Reaction time (min) | Conversion (%) | Reaction rate ($mol_{o\text{-}CNB}/mol_{Pt} \cdot s$) | Selectivity (%) | |
|---|---|---|---|---|---|---|
| | | | | | o-chloroaniline | aniline |
| 0.1 | 0.20 | 95 | 100 | 0.22 | >99.9 | 0.0 |
| 2.0 | 0.05 | 10 | 76.0 | 6.42 | >99.9 | 0.0 |
| | 0.05 | 10 | 89.4 | 7.55 | >99.9 | 0.0 |
| 4.0 | 0.05 | 20 | 100 | 7.60 | >99.9 | 0.0 |
| | 0.05 | 240 | 100 | — | >99.9 | 0.0 |

Reaction conditions: methanol, 25 ml; temperature, 333 K; o-CNB, 13.0 mmol.

Example 15

Selective Hydrogenation of p-CNB over Pt/γ-$Fe_2O_3$ 0.2 g of the Pt/γ-$Fe_2O_3$ nanocomposite containing 1 wt. % of Pt was dispersed in 5 ml of methanol, and activated at 333 K under 0.1 MPa of hydrogen pressure for 30 min, then 20 ml of methanol solution containing 1.27 mmol of p-CNB was added into the reactor. The reaction was conducted at 333 K under vigorously stirring. The products were analyzed by GC. The catalytic activity and selectivity over the catalyst are listed in TABLE 2. After the reaction was complete, the catalyst was separated from the reaction system in an applied magnetic field, washed with methanol, and reused in the next cycle of reaction without obvious change in the catalytic properties.

TABLE 2

| Catalyst (g) | Reaction time (min) | Conversion (%) | Selectivity (%) | |
|---|---|---|---|---|
| | | | p-chloroaniline | aniline |
| 0.20 | 45.3 | 100 | >99.9 | 0.0 |

Reaction conditions: methanol, 25 ml; temperature, 333 K; hydrogen pressure, 0.1 MPa; p-CNB, 1.27 mmol.

Example 16

Selective Hydrogenation of 2,4-dinitrochlorobenzene (2,4-DNCB) over Pt/γ-$Fe_2O_3$ 0.10 g of the Pt/γ-$Fe_2O_3$ nanocomposite containing 1 wt. % of Pt was dispersed in 5 ml of methanol, and activated at 333 K under 0.1 MPa of hydrogen pressure for 30 min, then 20 ml of methanol solution containing 1.27 mmol of 2,4-DNCB was added into the reactor. The reaction was conducted at 333 K under vigorously stirring. The products were analyzed by GC. The products were analyzed by GC. The catalytic activity and selectivity over the catalyst are listed in TABLE 3.

TABLE 3

| Catalyst (g) | Reaction time (min) | Conversion (%) | Reaction rate ($mol_{2,4\text{-}DNCB}/mol_{Pt} \cdot s$) | Selectivity (%) | |
|---|---|---|---|---|---|
| | | | | 4-chloro-m-phenylenediamine | m-phenylenediamine |
| 0.10 | 80 | 100 | 0.052 | >99.9 | 0.0 |

Reaction conditions: methanol, 25 ml; temperature, 333 K; hydrogen pressure, 0.1 MPa; 2,4-DNCB, 1.27 mmol.

Example 17

Selective Hydrogenation of o-bromonitrobenzene (o-BNB) over Pt/γ-$Fe_2O_3$ 0.04 g of the Pt/γ-$Fe_2O_3$ nanocomposite containing 1 wt. % of Pt was added into 100 ml of methanol solution containing o-BNB (0.10 mol/l), then the reaction was conducted at 303 K under 3.6 MPa of hydrogen pressure. The products were analyzed by GC. The catalytic activity and selectivity over the catalyst are listed in TABLE 4.

TABLE 4

| Catalyst (g) | Reaction time (min) | Conversion (%) | Selectivity (%) | |
|---|---|---|---|---|
| | | | o-bromoaniline | aniline |
| 0.04 | 20 | 100 | >99.0 | 0.0 |

Reaction conditions: methanol, 100 ml; temperature, 303 K; hydrogen pressure, 3.6 MPa; o-BNB, 10 mmol.

Example 18

Selective Hydrogenation of p-iodonitrobenzene (p-INB) over Pt/γ-$Fe_2O_3$ 0.15 g of the Pt/γ-$Fe_2O_3$ nanocomposite containing 1 wt. % of Pt was dispersed in 5 ml of THF, and activated at 303 K under 0.1 MPa of hydrogen pressure for 30 min, then 10 ml of THF solution containing p-INB (0.15 mol/l) was added into the reactor. The reaction was conducted at 303 K under vigorously stirring. The products were analyzed by GC. The catalytic activity and selectivity over the catalyst are listed in TABLE 5.

TABLE 5

| Catalyst (g) | Reaction time (min) | Conversion (%) | Selectivity (%) | |
|---|---|---|---|---|
| | | | p-iodoaniline | aniline |
| 0.15 | 45 | 100 | >99.0 | 0.0 |

Reaction conditions: THF, 15 ml; temperature, 303 K; hydrogen pressure, 0.1 MPa; p-INB, 1.5 mmol.

Example 19

Selective Hydrogenation of 3,4-dichloronitrobenzene (3,4-DCNB) over Pt/γ-Fe$_2$O$_3$ 0.2 g of the Pt/γ-Fe$_2$O$_3$ nanocomposite containing 1 wt. % of Pt was dispersed in 5 ml of methanol, and activated at 333 K under 0.1 MPa of hydrogen pressure for 30 min, then 20 ml of methanol solution containing 1.27 mmol of 3,4-DCNB was added into the reactor. The reaction was conducted at 333 K under vigorously stirring. The products were analyzed by GC. The catalytic activity and selectivity over the catalyst are listed in TABLE 6.

TABLE 6

| Catalyst (g) | Reaction time (min) | Conversion (%) | Reaction time (mol$_{3,4-DCNB}$/mol$_{Pt}$ · s) | Selectivity (%) | | |
|---|---|---|---|---|---|---|
| | | | | 3,4-dichloro-aniline | chloroaniline | aniline |
| 0.20 | 30 | 100 | 0.068 | >99.9 | 0.0 | 0.0 |

Reaction conditions: methanol, 25 ml; temperature, 333 K; hydrogen pressure, 0.1 MPa; 3,4-DCNB, 1.27 mmol.

Example 20

Selective Hydrogenation of 2-chloro-6-nitrotoluene over Pt/γ-Fe$_2$O$_3$ 0.2 g of the Pt/γ-Fe$_2$O$_3$ nanocomposite containing 1 wt. % of Pt was dispersed in 5 ml of methanol, and activated at 333 K under 0.1 MPa of hydrogen pressure for 30 min, then 20 ml of methanol solution containing 1.27 mmol of 2-chloro-6-nitrotoluene was added into the reactor. The reaction was conducted at 333 K under vigorously stirring. The products were analyzed by GC. The catalytic activity and selectivity over the catalyst are listed in TABLE 7.

TABLE 7

| Catalyst (g) | Reaction time (min) | Conversion (%) | Selectivity (%) | |
|---|---|---|---|---|
| | | | 3-chloro-2-methylaniline | o-methylaniline |
| 0.20 | 35 | 100 | >99.9 | 0.0 |

Reaction conditions: methanol, 25 ml; temperature, 333 K; hydrogen pressure, 0.1 MPa; 2-chloro-6-nitrotoluene, 1.27 mmol.

Example 21

Selective Hydrogenation of Methyl 4-chloro-3-nitrobenzoate over Pt/γ-Fe$_2$O$_3$ 0.2 g of the Pt/γ-Fe$_2$O$_3$ nanocomposite containing 1 wt. % of Pt was dispersed in 5 ml of methanol, and activated at 333 K under 0.1 MPa of hydrogen pressure for 30 min, then 20 ml of methanol solution containing 1.27 mmol of methyl 4-chloro-3-nitrobenzoate was added into the reactor. The reaction was conducted at 333 K under vigorously stirring. The products were analyzed by GC. The catalytic activity and selectivity over the catalyst are listed in TABLE 8.

TABLE 8

| Catalyst (g) | Reaction time (min) | Conversion (%) | Selectivity (%) | |
|---|---|---|---|---|
| | | | methyl 4-chloro-3-amino-benzoate | methyl 3-amino-benzoate |
| 0.20 | 50 | 100 | >99.9 | 0.0 |

Reaction conditions: methanol, 25 ml; temperature, 333 K; hydrogen pressure, 0.1 MPa; methyl 4-chloro-3-nitrobenzoate, 1.27 mmol.

Example 22

Selective Hydrogenation of 4-chloro-3-nitro-methoxybenzene over Pt/γ-Fe$_2$O$_3$ 0.2 g of the Pt/γ-Fe$_2$O$_3$ nanocomposite containing 1 wt. % of Pt was dispersed in 5 ml of methanol, and activated at 333 K under 0.1 MPa of hydrogen pressure for 30 min, then 30 ml of methanol solution containing 1.27 mmol of 4-chloro-3-nitro-methoxybenzene was added into the reactor. The reaction was conducted at 333 K under vigorously stirring. The products were analyzed by GC. The catalytic activity and selectivity over the catalyst are listed in TABLE 9.

TABLE 9

| Catalyst (g) | Reaction time (min) | Conversion (%) | Selectivity (%) | |
|---|---|---|---|---|
| | | | 4-chloro-3-amino-methoxy-benzene | 3-amino-methoxy-benzene |
| 0.20 | 55 | 100 | >99.9 | 0.0 |

Reaction conditions: methanol, 35 ml; temperature, 333 K; hydrogen pressure, 0.1 MPa; 4-chloro-3-nitro-methoxybenzene, 1.27 mmol.

Example 23

Selective Hydrogenation of 4-chloro-3-nitro-diphenyl over Pt/γ-Fe$_2$O$_3$ 0.2 g of the Pt/γ-Fe$_2$O$_3$ nanocomposite containing 1 wt. % of Pt was dispersed in 5 ml of THF, and activated at 333 K under 0.1 MPa of hydrogen pressure for 30 min, then 30 ml of THF solution containing 1.27 mmol of 4-chloro-3-nitro-diphenyl was added into the reactor. The reaction was conducted at 333 K under vigorously stirring. The products were analyzed by GC. The catalytic activity and selectivity over the catalyst are listed in TABLE 10.

TABLE 10

| Catalyst (g) | Reaction time (min) | Conversion (%) | Selectivity (%) | |
|---|---|---|---|---|
| | | | 4-chloro-3-amino-diphenyl | 3-amino-diphenyl |
| 0.20 | 70 | 100 | >99.9 | 0.0 |

Reaction conditions: THF, 35 ml; temperature, 333 K; hydrogen pressure, 0.1 MPa; 4-chloro-3-nitro-diphenyl, 1.27 mmol.

Example 24

Selective Hydrogenation of 4-chloro-3-nitro-4'-methyldiphenyl over Pt/γ-Fe$_2$O$_3$ 0.2 g of the Pt/γ-Fe$_2$O$_3$ nanocomposite containing 1 wt. % of Pt was dispersed in 5 ml of toluene, and activated at 383 K under 0.1 MPa of hydrogen pressure for 30 min, then 30 ml of toluene solution containing 1.27 mmol of 4-chloro-3-nitro-4'-methyldiphenyl was added into the reactor. The reaction was conducted at 383 K under vigorous stirring. The products were analyzed by GC. The catalytic activity and selectivity over the catalyst are listed in TABLE 11.

TABLE 11

| Catalyst (g) | Reaction time (min) | Conversion (%) | Selectivity (%) | |
|---|---|---|---|---|
| | | | 4-chloro-3-amino-4'-methyldiphenyl | 3-amino-4'-methyldiphenyl |
| 0.20 | 70 | 100 | >99.9 | 0.0 |

Reaction conditions: toluene, 35 ml; temperature, 383 K; hydrogen pressure, 0.1 MPa; 4-chloro-3-nitro-4'-methyldiphenyl, 1.27 mmol.

Example 25

Selective Hydrogenation of 4-chloro-3-nitro-4'-methyl-3'-nitro-diphenyl over Pt/γ-Fe$_2$O$_3$ 0.2 g of the Pt/γ-Fe$_2$O$_3$ nanocomposite containing 1 wt. % of Pt was dispersed in 5 ml of THF, and activated at 333 K under 0.1 MPa of hydrogen pressure for 30 min, then 50 ml of THF solution containing 1.27 mmol of 4-chloro-3-nitro-4'-methyl-3'-nitro-diphenyl was added into the reactor. The reaction was conducted at 333 K under vigorous stirring. The products were analyzed by GC. The catalytic activity and selectivity over the catalyst are listed in TABLE 12.

TABLE 12

| Catalyst (g) | Reaction time (min) | Conversion (%) | Selectivity (%) | |
|---|---|---|---|---|
| | | | 4-chloro-3-amino-4'-methyl-3'-amino-diphenyl | 4-methyl-3-amino-3'-amino-diphenyl |
| 0.20 | 90 | 100 | >99.9 | 0.0 |

Reaction conditions: THF, 55 ml; temperature, 333 K; hydrogen pressure, 0.1 MPa; 4-chloro-3-nitro-4'-methyl-3'-nitro-diphenyl, 1.27 mmol.

Example 26

Selective Hydrogenation of p-CNB over the Pt/Magnetic Iron Oxides Nanocomposite 0.1 g of the Pt/magnetic iron oxides nanocomposite containing 3 wt. % of Pt prepared in Example 7 was dispersed in 5 ml of methanol, and activated at 333 K under 0.1 MPa of hydrogen pressure for 30 min, then 20 ml of methanol solution containing 1.27 mmol of p-CNB was added into the reactor. The reaction was conducted at 333 K under vigorously stirring. The products were analyzed by GC. The catalytic activity and selectivity over the catalyst are listed in TABLE 13.

TABLE 13

| Catalyst (g) | Reaction time (min) | Conversion (%) | Selectivity (%) | |
|---|---|---|---|---|
| | | | p-chloroaniline | aniline |
| 0.10 | 31 | 100 | >99.9 | 0.0 |

Reaction conditions: methanol, 25 ml; temperature, 333 K; hydrogen pressure, 0.1 MPa; p-CNB, 1.27 mmol.

Example 27

Selective Hydrogenation of m-CNB over the Pt/Magnetic Iron Oxides Nanocomposite 0.2 g of the Pt/magnetic iron oxides nanocomposite prepared in Example 13 was dispersed in 5 ml of methanol, and activated at 333 K under 0.1 MPa of hydrogen pressure for 30 min, then 20 ml of methanol solution containing 1.27 mmol of m-CNB was added into the reactor. The reaction was conducted at 333 K under vigorously stirring. The products were analyzed by GC. The catalytic activity and selectivity over the catalyst are listed in TABLE 14.

TABLE 14

| Catalyst (g) | Reaction time (min) | Conversion (%) | Selectivity (%) | |
|---|---|---|---|---|
| | | | m-chloroaniline | aniline |
| 0.20 | 43 | 100 | >99.9 | 0.0 |

Reaction conditions: methanol, 25 ml; temperature, 333 K; hydrogen pressure, 0.1 MPa; m-CNB, 1.27 mmol.

Example 28

Selective Hydrogenation of p-CNB over Pt—Pd/γ-Fe$_2$O$_3$ 0.2 g of the Pt—Pd/γ-Fe$_2$O$_3$ nanocomposite with 1 wt. % of metal loading and a Pt/Pd molar ratio of 4:1 prepared in Example 12 was dispersed in 5 ml of methanol, and activated at 333 K under 0.1 MPa of hydrogen pressure for 30 min, then 20 ml of methanol solution containing 1.27 mmol of p-CNB was added into the reactor. The reaction was conducted at 333 K under vigorously stirring. The products were analyzed by GC. The catalytic activity and selectivity over the catalyst are listed in TABLE 15.

TABLE 15

| Catalyst (g) | Reaction time (min) | Conversion (%) | Selectivity (%) | |
|---|---|---|---|---|
| | | | p-chloroaniline | aniline |
| 0.20 | 41 | 100 | >99.9 | 0.0 |

Reaction conditions: methanol, 25 ml; temperature, 333 K; hydrogen pressure, 0.1 MPa; p-CNB, 1.27 mmol.

Example 29

Selective Hydrogenation of p-CNB over Pt—Ru/γ-Fe$_2$O$_3$ 0.2 g of the Pt—Ru/γ-Fe$_2$O$_3$ nanocomposite with 1 wt. % of metal loading and a Pt/Ru molar ratio of 1:1 prepared in Example 9 was dispersed in 5 ml of methanol, and activated at 333 K under 0.1 MPa of hydrogen pressure for 30 min, then 20 ml of methanol solution containing 1.27 mmol of p-CNB was added into the reactor. The reaction was conducted at 333 K under vigorously stirring. The products were analyzed by GC. The catalytic activity and selectivity over the catalyst are listed in TABLE 16.

TABLE 16

| Catalyst | Reaction time | Conversion | Selectivity (%) | |
|---|---|---|---|---|
| (g) | (min) | (%) | p-chloroaniline | aniline |
| 0.20 | 58 | 100 | >99.9 | 0.0 |

Reaction conditions: methanol, 25 ml; temperature, 333 K; hydrogen pressure, 0.1 MPa; p-CNB, 1.27 mmol.

Example 30

Selective Hydrogenation of p-CNB over Pt—Os/γ-Fe$_2$O$_3$ 0.2 g of the Pt—Os/γ-Fe$_2$O$_3$ nanocomposite with 1 wt. % of metal loading and a Pt/Os molar ratio of 20:1 prepared by the same method described in Example 9 was dispersed in 5 ml of methanol, and activated at 333 K under 0.1 MPa of hydrogen pressure for 30 min, then 20 ml of methanol solution containing 1.27 mmol of p-CNB was added into the reactor. The reaction was conducted at 333 K under vigorously stirring. The products were analyzed by GC. The catalytic activity and selectivity over the catalyst are listed in TABLE 17.

TABLE 17

| Catalyst | Reaction time | Conversion | Selectivity (%) | |
|---|---|---|---|---|
| (g) | (min) | (%) | p-chloroaniline | aniline |
| 0.20 | 79 | 100 | >99.9 | 0.0 |

Reaction conditions: methanol, 25 ml; temperature, 333 K; hydrogen pressure, 0.1 MPa; p-CNB, 1.27 mmol.

Example 31

Selective Hydrogenation of p-CNB over Pt—Ir/γ-Fe$_2$O$_3$ 0.2 g of the Pt—Ir/γ-Fe$_2$O$_3$ nanocomposite with 1 wt. % of metal loading and a Pt/Ir molar ratio of 1:1 prepared in Example 10 was dispersed in 5 ml of methanol, and activated at 333 K under 0.1 MPa of hydrogen pressure for 30 min, then 20 ml of methanol solution containing 1.27 mmol of p-CNB was added into the reactor. The reaction was conducted at 333 K under vigorously stirring. The products were analyzed by GC. The catalytic activity and selectivity over the catalyst are listed in TABLE 18.

TABLE 18

| Catalyst | Reaction time | Conversion | Selectivity (%) | |
|---|---|---|---|---|
| (g) | (min) | (%) | p-chloroaniline | aniline |
| 0.20 | 62 | 100 | >99.9 | 0.0 |

Reaction conditions: methanol, 25 ml; temperature, 333 K; hydrogen pressure, 0.1 MPa; p-CNB, 1.27 mmol.

The experimental results of this section show that, the nanocomposite catalysts according to the present invention possess high catalytic activity and superior selectivity for the hydrogenation of aromatic halonitro compounds to the corresponding aromatic haloamines. The hydrodehalogenation side reaction is fully inhibited successfully over the invented nanocomposite catalysts, indicating that these catalysts can be used for efficiently producing aromatic haloamines with a high purity.

INDUSTRIAL APPLICATION

In virtue of the catalytic function of the metal nanoclusters, the present invention succeeded in preparing a new kind of magnetic transition metals-iron oxides nanocomposite materials at relative low temperature. The main features of the preparation method according to the present invention are first to prepare the colloidal solutions of "unprotected" transition metal or alloy nanoclusters, which are then mixed with the colloidal solutions of ferric hydroxide nanoparticles to form complex sols, followed by the heat treatment in the presence of reductants, such as alcohol, aldehyde and glycolic acid. The obtained products are washed, dried or oxidized to produce the said nanocomposite materials composed of the transition metal nanoclusters and magnetic iron oxides nanoparticles.

The invented nanocomposite materials composed of transition metal nanoclusters and magnetic iron oxides nanoparticles can catalyze the hydrogenation of aromatic halonitro compounds to aromatic haloamines with very high selectivity. The hydrodehalogenation side reaction in the hydrogenation of aromatic halonitro compounds to aromatic haloamines was fully suppressed for the first time over the present nanocomposite catalysts. Moreover, due to the two or more functional components and the cooperative effect between the nanoparticles, the invented nanocomposite materials are of great value for application in the fields of catalyst, magnetic separation, wave-absorption materials, etc.

We claim:

1. Transition metals-magnetic iron oxides nanocomposite materials consisting of a composite of transition metals or alloys thereof nanoparticles having a diameter ranging from 0.7 to 5 nm and magnetic iron oxides nanoparticles having a diameter ranging from 5 to 50 nm, the total content of the transition metals or the alloys thereof in the nanocomposite materials ranging from 0.1 to 30 wt. %, the magnetic iron oxides including γ-Fe$_2$O$_3$ and Fe$_3$O$_4$, the composite made from part reduction of the γ-Fe$_2$O$_3$ and part oxidation of Fe$_3$O$_4$.

2. The nanocomposite materials according to claim 1, wherein the composite derived from part reduction of γ-Fe$_2$O$_3$ is obtained by partly reducing the transition metal-γ-Fe$_2$O$_3$ nanocomposite at 278-473 K in the presence of a reductant selected from the group consisting of hydrogen, glycolic acid, alcohol, aldehyde and mixtures thereof.

3. The nanocomposite materials according to claim 1, wherein the composite derived from part oxidation of Fe$_3$O$_4$ is obtained by partly oxidizing the transition metal-$Fe_3O_4$ nanocomposite at 313-523 K in the presence of oxygen.

4. The nanocomposite materials according to claim 1, wherein the transition metals are selected from the group consisting of Pt, Ru, Rh, Os and Ir; and the transition metal alloys are composed of at least two metal elements selected from the group consisting of Pt, Pd, Ru, Rh, Os and Ir.

5. The nanocomposite materials according to claim 1, wherein the diameter of the magnetic iron oxide nanoparticles ranges from 5 to 25 nm.

6. A method for producing the nanocomposite materials of claim 1 comprising the steps of:
   1) preparing a transition metal colloid by dissolving at least one soluble salt or acid containing a transition metal into an alcohol solution or alcohol/water mixture to form transition metal compound solution with a concentration of 0.01-100 g/l;
      mixing an alcohol solution, or aqueous solution, or alcohol/water containing an alkali metal hydroxide or alkaline-earth metal hydroxide into the transition metal compound solution;
      heating the obtained mixture at 343-473 K to produce a colloidal solution of transition metal nanoclusters, the colloidal solution of transition metal nanoclusters having a molar ratio of alkali metal hydroxides or alkaline-earth metal hydroxides to the salt or acid containing the transition metal from between 3 to 30;
      wherein the alcohols are selected from the group consisting of alcohols containing 1-8 carbon atoms and one, two, or three hydroxyl groups, and their derivatives containing one methoxyl or ethoxyl group; and the typical volume content of water in the alcohol/water mixtures is between 0-50%;
   2) preparing a ferric hydroxide colloid by forming a precipitate of ferric hydroxide by adding an alkaline solution into a solution containing an $Fe^{3+}$ salt and adjusting the pH value to between 4-12;
      peptizing the obtained precipitate in a peptizing agent to produce a colloidal solution of ferric hydroxide with a concentration of 1-300 g/l;
      wherein the said peptizing agents are selected from the group consisting of ferric chloride solution, ferric nitrate solution and hydrochloric acid;
   3) preparing a nanocomposite material having transition metal nanoclusters and magnetic iron oxide nanoparticles by mixing the transition metal colloidal solution prepared in step 1) and the ferric hydroxide colloidal solution prepared in step 2) at a mass ratio of metal colloidal solution to ferric hydroxide colloidal solution between 1:3-1:13400;
      heat treating the mixture at 313-523 K between 1-200 h; and
      drying the mixture at 313-523 K for the purpose of providing a nanocomposite material having transition metal nanoclusters and magnetic iron oxide nanoparticles.

7. The preparation method according to claim 6, wherein the soluble salt or acid containing the transition metal in step 1) is selected from the group consisting of a salt or acid containing Pt, Pd, Ru, Rh, Os or Ir.

8. The preparation method according to claim 6, wherein the concentration of the $Fe^{3+}$ salt in the solution of step 2) is between 0.01-4 mol/l;
   the alkali metal hydroxide or alkaline-earth metal hydroxide is selected from the group consisting of ammonia, potassium hydroxide, sodium hydroxide, lithium hydroxide, tetramethylammonium hydroxide, and butylamine;
   the temperature for precipitating ferric hydroxide is between 278-370 K;
   the concentration of peptizing agents is in the range of 0.01-2 mol/l; and
   the peptizing in step 2) is conducted at a temperature between 278-373 K.

9. The preparation method according to claim 6, wherein the heat treating in step 3) is selected from the group consisting of a solvothermal method, a heating and refluxing method, and a microwave irradiation method.

10. The preparation method according to claim 6, wherein the drying process is selected from the group of drying processes consisting of drying the precipitates at 313-523 K in vacuum to obtain transition metal-$Fe_3O_4$ nanocomposite materials, drying and oxidizing the precipitates in oxygen-containing atmosphere to produce transition metal-$\gamma$-$Fe_2O_3$ nanocomposite materials and drying and partly oxidizing the precipitates in oxygen-containing atmosphere to produce transition metal-magnetic iron oxides nanocomposite materials, the magnetic iron oxide being produced by partly oxidating the $Fe_3O_4$.

11. The preparation method according to claim 10, wherein the transition metal-$\gamma$-$Fe_2O_3$ nanocomposite is reduced at a temperature between 278-473 K using a reductant selected from the group consisting of hydrogen, glycolic acid, alcohol and aldehyde.

12. A method for producing the nanocomposite materials of claim 1 comprising the steps of:
   1) preparing a transition metal colloids by dissolving at least one soluble salt or acid containing a transition metal into an alcohol solution or alcohol/water mixture to form a transition metal compound solution with a concentration of 0.01-100 g/l;
      adding mixing an alcohol solution, or aqueous solution, or alcohol/water mixture containing an alkali metal hydroxide or alkaline-earth metal hydroxide into the transition metal compound solution;
      wherein the molar ratio of alkali metal hydroxide or alkaline-earth metal hydroxide to the salt or acid containing the transition metal in the range of 3 to 30, the alcohols selected from the group consisting of alcohols containing 1-8 carbon atoms and one, two, or three hydroxyl groups, and their derivatives containing one methoxyl or ethoxyl group and the volume content of water in the alcohol/water mixtures is between 0-50%;
      heating the mixture between 373-473 K;
      adding an acidic aqueous solution to form a precipitate of transition metal nanoclusters
      dispersing the precipitate of transition metal nanoclusters into an ethylene glycol solutions containing an alkali metal hydroxide or alkaline-earth metal hydroxide, or into another organic solvent, in order to produce a colloidal solution of transition metal nanoclusters;
      wherein the organic solvents are selected from the group consisting of alcohols containing two or three hydroxyl groups and 1-8 carbon atoms, ketone, 1,4-dioxane, DMSO, THF and DMF;
   2) preparing a ferric hydroxide colloid by forming a precipitate of ferric hydroxide by adding an alkaline solution into a solution containing $Fe^{3+}$ salts to adjust the pH value to 4-12;

peptizing the precipitate of ferric hydroxide in peptizing agents to produce a colloidal solution of ferric hydroxide with a concentration of 1-300 g/l the peptizing agents selected from the group consisting of ferric chloride solution, ferric nitrate solution and hydrochloric acid; and 3) preparing a nanocomposite material having transition nanoclusters and magnetic iron oxide nanoparticles;

mixing the transition metal colloidal solution prepared in step 1) with the ferric hydroxide colloidal solution prepared in step 2) at a mass ratio of metal colloidal solution to ferric hydroxide colloidal solution of between 1:3-1:13400;

adding an organic reductant to the mixture;

heat treating the mixture with the organic reductant at a temperature between 313-523 K for 1-200 h; and drying the mixture with the organic reductant at a temperature between 313-523 K, in order to provide the nanocomposite material composed of transition metal nanoclusters and magnetic iron oxide nanoparticles;

wherein the organic reductant is selected from the group consisting of formaldehyde, glycolic acid, sodium glycolate, isopropyl alcohol, glyoxal, oxalic acid and hydrogen.

13. The preparation method according to claim 12, wherein the soluble salt or acid containing the transition metal in step 1) are selected from a salt or acid containing an element selected from the group consisting of Pt, Pd, Ru, Rh, Ir and Os.

14. The preparation method according to claim 12, wherein the concentration of the $Fe^{3+}$ salts in the solutions is 0.01-4 mol/l;

the alkali metal hydroxide or alkaline-earth metal hydroxide is selected from the group consisting of ammonia, potassium hydroxide, sodium hydroxide, lithium hydroxide, and tetramethylammonium hydroxide;

the ferric hydroxide is precipitated at a temperature between 278-370 K;

the concentration of peptizing agents is in the range of 0.01-2 mol/l; and the precipitate of ferric hydroxide is peptized at a temperature between 278-373 K.

15. The preparation method according to claim 12, wherein the molar ratio of the organic reductant to ferric hydroxide in step 3) is between 0.1-10.

16. The preparation method according to claim 12, wherein the heat treating in step 3) is selected from the group consisting of a solvothermal method, a heating and refluxing method, and a microwave irradiation method.

17. The preparation method according to claim 12, wherein the drying process in step 3) conducted by a drying process selected from the group consisting of drying the precipitates at 313-523 K in vacuum to obtain a transition metal-$Fe_3O_4$ nanocomposite material, drying and oxidizing the precipitates in an oxygen-containing atmosphere to produce a transition metal-$\gamma$-$Fe_2O_3$ nanocomposite material, and drying and partly oxidizing the precipitates in an oxygen-containing atmosphere to produce a transition metal-magnetic iron oxide nanocomposite material, the magnetic iron oxide being produced by partly oxidizing $Fe_3O_4$.

18. The preparation method according to claim 17, wherein the transition metal-$\gamma$-$Fe_2O_3$ nanocomposite is reduced at a temperature between 278-473 K using a reductant selected from the group consisting of hydrogen, glycolic acid, alcohol and aldehyde.

* * * * *